United States Patent [19]

Sahota

[11] Patent Number: 4,509,528
[45] Date of Patent: Apr. 9, 1985

[54] HEMOSTAT WITH BLOOD FLOW SENSOR

[76] Inventor: Harvinder Sahota, 3861 Wisteria, Seal Beach, Calif. 90740

[21] Appl. No.: 398,621

[22] Filed: Jul. 15, 1982

Related U.S. Application Data

[63] Continuation-in-part of Ser. No. 331,236, Dec. 16, 1981.

[51] Int. Cl.³ .......................... A61B 5/02; A61B 17/12
[52] U.S. Cl. .................................. 128/691; 128/325; 128/346
[58] Field of Search ............... 128/325, 327, 346, 691, 128/662, 663

[56] References Cited

U.S. PATENT DOCUMENTS

| | | | |
|---|---|---|---|
| 3,625,219 | 12/1971 | Abrams | 248/125 X |
| 3,884,240 | 5/1975 | Gilman | 128/325 |
| 4,154,231 | 5/1979 | Russell | 128/663 |
| 4,321,929 | 3/1982 | Lemelson et al. | 128/691 X |

Primary Examiner—Michael H. Thaler
Attorney, Agent, or Firm—Knobbe, Martens, Olson & Bear

[57] ABSTRACT

A hemostat for restricting blood flow through a blood vessel for assisting hemostasis. An ultrasonic sensor is mounted with a pressure pad to sense rate of blood flow through the vessel when pressure is applied to obtain minimum bleeding with maximum flow through the vessel, without need for continual observation. The output signal of the sensor may be connected to an auditory signal or a visual display to free personnel from the site to perform other necessary tasks.

27 Claims, 8 Drawing Figures

HEMOSTAT WITH BLOOD FLOW SENSOR

BACKGROUND OF THE INVENTION

This is a continuation-in-part of the applicant's prior copending application Ser. No. 331,236 filed Dec. 16, 1981 for Hemostat with Blood Flow Sensor.

Many medical tests require the insertion of a catheter into an artery. The catheter is normally inserted through a percutaneous puncture made through the wall of the artery and pushed into the artery to a desired position. Catheterization techniques may be employed for such various procedures as heart blood pressure analysis, dialysis, arterial blood gas assays, and visualization of vascular location for X-rays.

Upon removing the catheter from the artery, the puncture in the arterial wall must be closed to stop bleeding. Since the puncture site is small, as is the size of the artery itself, the use of sutures is cumbersome and possibly dangerous. Most often, blood flow through the artery is restricted to reduce bleeding through the puncture so a clot may form at the puncture site and close the opening. This technique requires application of pressure to the artery upstream of the puncture site to reduce blood flow for a sufficiently long time for a clot to form and become attached to the wall of the artery. Pressure must be applied to the artery from ten to twenty minutes on the average, and at times for a longer period.

In the past, finger pressure was applied to the artery, which frequently required the use of both hands for effective compression and also required a reasonable degree of skill in order to apply the proper amount of pressure required without collapsing the artery. It was necessary for a trained person to remain at the puncture site until a clot was formed and bleeding stopped.

Many problems were inherent in this procedure. Because it is tedious to apply pressure to the wound site for such a long period of time, the finger pressure applied was unsteady and there was a danger of collapsing the artery completely by the application of too much pressure. Collapsing the artery could result in the formation of thrombosis in the collapsed region, which could completely and permanently block the artery, requiring subsequent surgical procedures to relieve the blockage. In certain procedures, such as heart catheterization, which require insertion of a catheter into the femoral artery, which feeds blood to the leg, serious damage including gangrene and resultant amputation is possible by cessation of blood flow for too long a period. As best, thrombosis may form; or muscular spasms may result, causing complications.

Secondarily, having a trained person remain at the puncture site for the prolonged period required for clot formation is unproductive. The person should be performing other necessary tasks. Also, the trained person may be hindered from rendering emergency care to the patient should an emergency situation arise.

To solve these problems, mechanical devices have been developed for applying pressure to an artery to obtain hemostasis, allowing trained personnel to attend to other duties. U.S. Pat. No 3,779,249 shows a C-clamp device having a large disc-shaped pad attached to the end of a cantilevered arm which extends over a patient lying below. The arm and pad are lowered so that the pad will cover the puncture site upon withdrawal of the catheter until a clot in the puncture is obtained. During use, the C-clamp device exerts a non-calibrated and uneven pressure directly on the area of the puncture site to restrict bleeding. The pad covers the puncture, preventing a doctor from viewing the puncture site to determine whether bleeding has been stopped and to watch the progression of clot formation in the puncture. This clamp device provides only vertical movement of the arm and pad, which makes adjustment to the location of the puncture difficult. The large area of the pad covering the puncture site applies pressure to a substantially larger area than to the artery alone. This large pad, in combination with the crude sliding adjustment, makes accurate pressure application to the artery difficult and provides poor control to restrict blood flow. Use of this device still requires the constant attention of a physician, or other trained person, to control bleeding. This device provides little advantage over the application of finger pressure to an artery and, in fact, can cause a false sense of security in personnel which use it.

Other devices have been constructed which use a large inflated and flexible pad to cover the catheter entry site. One example, shown in U.S. Pat. No. 3,625,219 has a perpendicular rod assembly which is universally adjustable. Once positioned, the pad assembly is held in position by screw clamps. A pad positioned at a distal end of a horizontal rod or arm has a transparent rubber membrane clamped beneath a transparent plastic base. Air, or other fluid, is injected into the chamber between the base and membrane to expand the membrane outwardly to apply pressure over the arterial opening. Once the pad is inflated to apply pressure to the puncture area, the applied pressure may be determined by observation of a gauge connected to the chamber inlet. Pulsing indication of the blood pressure within the artery is also indicated on the pressure gauge. However, such pressure indications are not very accurate. The inflatable pad of this device overlies a large area surrounding the artery, so that, even though the pad elements are transparent, observation of the amount of bleeding and clot formation are obscured. The size of the pad makes it difficult to apply pin-point and accurate pressure to the artery. Pressure can be applied unevenly to the artery, possible leading to a hematoma of the arterial wall. Further, this device also requires a physician or technician to remain with the device to control the amount of air introduced into the chamber and to observe the pressure gauge. The clamp for maintaining adjustment of pressure applied to the artery by the pad is undependable and may be disturbed, thereby changing the pressure applied and allowing increased bleeding.

A second inflated pad device, shown in U.S. Pat. No. 4,233,890, also comprising a universally adjustable arm mechanism, has a pillow-like pressure pad similar to that disclosed in U.S. Pat. No. 3,625,219 mounted to a distal end of an extending arm. This device suffers from the same inadequacies of the device mentioned above and is of little advantage over the first C-clamp device described. There is no accurate way to control the pressure applied to the artery by this device or to accurately control the restriction of blood flow through the artery. There is no way to assure uniform distribution of pressure in the artery. Nor is there any way to clearly visualize the area surrounding the artery to determine the amount of bleeding or the advancement of clot formation. This device also requires constant supervision.

It can be seen that none of the prior devices provide for an accurate and dependable control of blood flow through an artery to reduce bleeding of a puncture in order for a clot to be formed; nor do any teach a means for sensing blood flow in the artery. These devices all require continual visual attention of a person for the duration of time required for clot formation, thereby preventing their attention to other tasks.

SUMMARY OF THE INVENTION

This invention provides a hemostatic device to control bleeding of any percutaneous vascular entry which can accurately apply a desired pressure locally to a blood vessel, without need of special assistance from or supervision of attending personnel. The capability of this device arises from a blood flow sensing means which determines the flow rate of blood through the vessel, and which produces an output signal which can be used to signal supervising personnel. The flow sensing means provides an accurate indication of blood flow and restriction of the blood vessel to all personnel present, without requiring their constant attention. The device further comprises an accurate means of adjusting pressure applied to a blood vessel, including an indicator for determining the clamping pressure. The hemostat may include a means for indicating systolic and diasytolic blood pressure supplied to the artery at the site of restriction.

A small changeable pressure pad is provided to apply firm and uniform pressure across the width of the artery upstream of a puncture, within a localized area. The pressure pad is removable for ease of selection to adapt a proper size relative to the size of the artery, and for ease of sterilization. The pressure pad is provided with a sensor which is connected with the flow sensing means for fast and accurate sensing of changes in the blood flow through an artery against which it is positioned.

In preferred form, the flow sensing means provides an auditory signal which changes in pitch or volume in response to changes in blood flow through the artery. The auditory signal allows all personnel in the area to hear a change in blood flow through the artery, thereby obviating need of constant supervision of the hemostat, though immediately indicating a problem to those present. The flow sensing means can also be connected to a video scanner to visually display changes in blood flow through the artery, or to a chart recorder to obtain a permanent record or arterial flow.

This hemostatic device allows for accurate control of bleeding through a puncture site and can be effectively used to speed clot formation in closure of the puncture. The accurate control of pressure applied locally to the artery provides means for minimizing bleeding through the puncture while maintaining maximum flow of blood through the artery to the dependent extremity. The sensor in the pressure pad and the flow sensing means provide an accurate indication of flow through the artery, thereby signaling when a problem should occur. An attending physician or technician will immediately be made aware so that emergency action can be taken. Further, an accurate means for obtaining a measurement of pressure applied on the artery is provided to assist a user in setting the device to restrict arterial flow, and assure that the artery will not be collapsed.

DESCRIPTION OF THE PREFERRED EMBODIMENT

Figure 1:
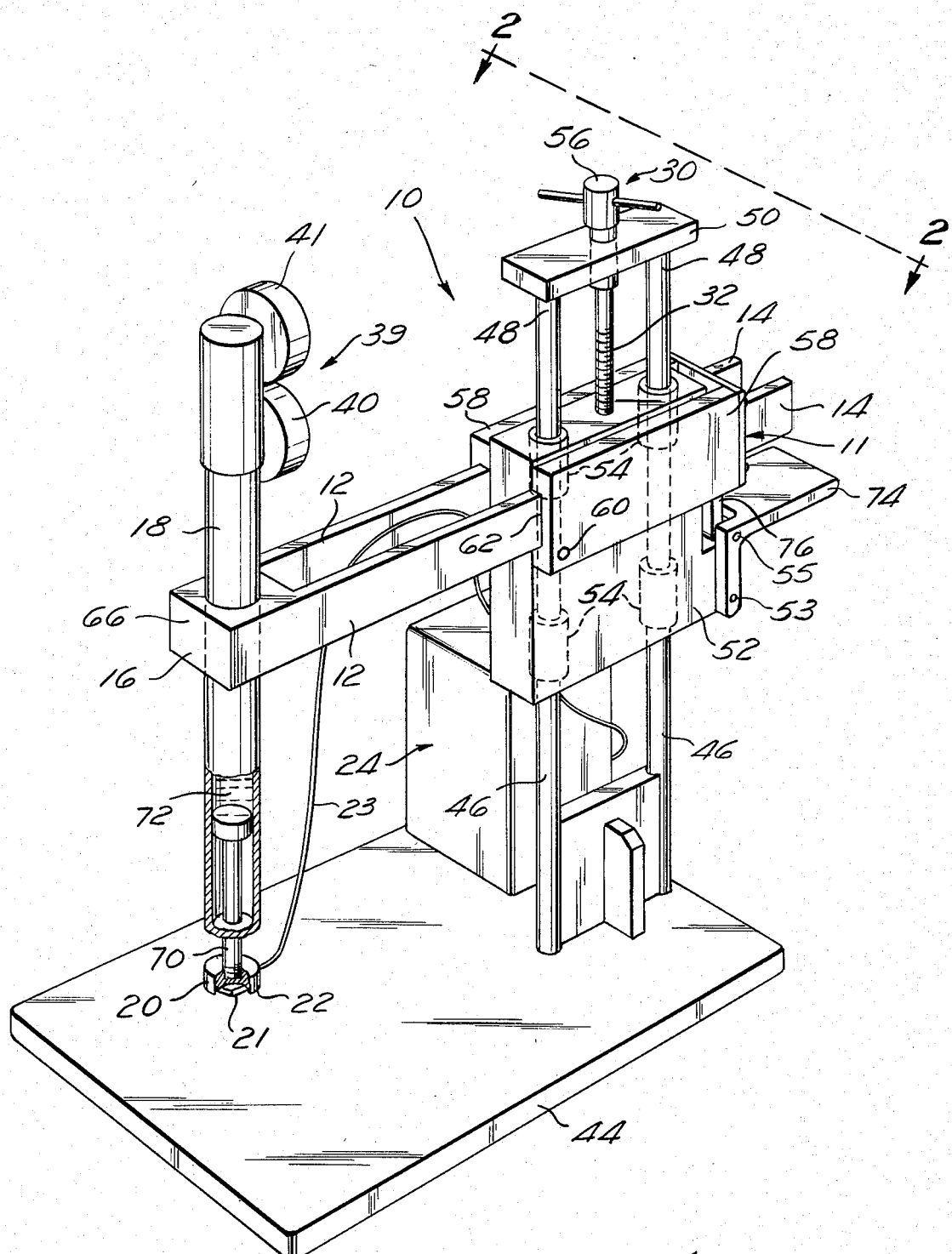
FIG. 1 is a forward perspective view of a hemostat having a blood flow sensing means, including a cutaway of a pressure pad holding member.
Figure 2:
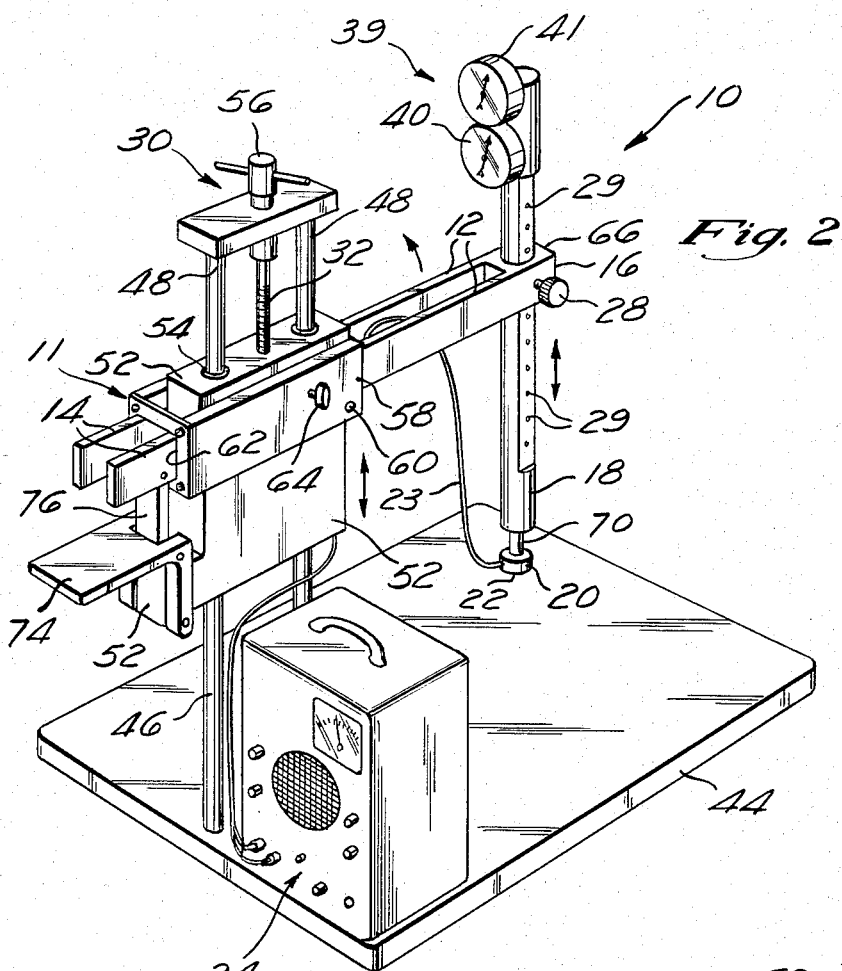
FIG. 2 is a rearward perspective view of a hemostat having a blood flow sensing means.

Referring to FIGS. 1 and 2, a hemostat 10 for restricting blood flow in a blood vessel to control bleeding through a percutaneous puncture is generally illustrated. A mounting fixture, generally indicated as 11, mounts horizontally extending arms 12 and cantilevers the arms 12 from a first end 14 outwardly from the mounting fixture 11. A pressure pad holding member 18 is mounted to a distal opposing end 16 of the arms 12. The holding pressure pad member 18 holds a pressure pad 20 at a lower portion and positions the pressure pad 20 in a generally downward position to engage a blood vessel of a patient lying thereunder. The pressure pad 20 of the hemostat is positioned upstream of the puncture to apply a pressure force against the wall of the blood vessel to constrict blood flow through the vessel and limit bleeding through the puncture.

The pressure pad 20 includes a sensor 21, as shown in FIG. 1, for detecting the flow of blood through a blood vessel. In preferred form, the sensor 21 comprises an ultrasonic signal generator and a doppler transducer which measure the velocity of a patient's blood flow by transmitting an ultrasonic signal through the blood and detecting the reflected signal, or echo. The frequency of the echo signal will be different from that of the original signal due to the doppler effect produced by the moving blood. The difference in frequencies between the original and reflected signals can be used to calculate the velocity of the blood flow and to provide an output signal corresponding to blood flow and changes in blood flow. The signal generator and transducer are encapsulated in an epoxy material to form the sensor 21. The sensor 21 is fastened within a small recess in the pressure pad 20, formed centrally in a face 22 of the pressure pad 20 applied against the artery. The sensor 21 may be either flush with the face 22 of the pressure pad 20 or recessed approximately one to two millimeters in order to produce the highest signal output in response to pulsating blood flow. The angular orientation of the sensor 21 relative to the face 22 is selected to maximize the sensor output signal.

The sensor 21 may, however, comprise an optical doppler apparatus, a transducer for photoplethysmography, a transducer for impedance plethysmography, a magnetodynamic blood flow probe for magnetic flow measurement techniques, or other non-occlusive flow sensing means. All of above-mentioned sensor devices are well known in the art and are extremely accurate in determining the rate flow of blood through a blood vessel.

The output signal provided by the sensor is directed through connectors 23 to a signal processor generally shown as 24, which analyzes the output signal produced by the sensor 21 and produces a second output signal, preferably a sound which varies in pitch or volume in response to changes in blood flow through the blood vessel. The ultrasonic sensor 21 and signal processor 24 herein described for determining a doppler effect response to blood flow are well known in the art of medical instrumentation. Such devices which function satisfactorily in the hemostat 10 are model numbers 812 and 841 marketed by Park Electronic Laboratories of Beaverton, Oreg.

The second output signal may, however, be directed to a video display to visually depict the blood flow rate and change of blood flow rate in the vessel, or to a chart recorder which provides a permanent record of blood flow rate through the blood vessel.

The pressure pad 20 is a generally disc-shaped plate having a substantially hard surface for applying pressure to the vessel. The pressure pad 20 is provided in a selection of sizes so that a proper width may be selected to closely approximate the width of the blood vessel to which it will apply pressure. Proper sizing of the pressure pad 20 applies pressure only locally to the vessel in which blood flow is to be restricted, and not to the surrounding tissue areas. Proper sizing of the pressure pad 20 provides for accurate control of blood flow restrictions and accurate positioning of the pressure pad 20 over the vessel to prevent the occurrence of problems, such as hematoma caused by uneven pressure. The pressure pad 20 is removable from the holding member 18 for each of replacement and for sterilization, and may be made disposable.

Referring to FIG. 2, the pressure exerted on the blood vessel by the pressure pad 20 is accurately controlled by adjustments provided in the hemostat 10 to accurately limit blood flow. The pressure pad holding member 18 is incrementally adjustable by a detent pin 28 positioned through the arm 12, which is adapted to engage one of a number of detent holes 29 in the holding member 18. The first incremental adjustment permits large segmented adjustments of the pressure pad holding member 18 relative to the distal end of the arm 12 to which it is mounted to allow large adjustments in the position of the pressure pad 20 relative to the artery which it will compress.

A substantially infinitely fine screw adjustment, generally shown as 30, is used after the incremental adjustment to make small precise movements of the pressure pad 20 to determine the exact pressure desired applied to the artery, and to accurately restrict blood flow through the artery by the desired amount. The fine screw adjustment 30 is preferably provided by a fine-threaded screw 32 which moves the arm 12, pressure pad 20 and holding member 18 relative to the blood vessel which is compressed.

An indicating instrument 39 indicates pressure exerted by the pressure pad 20 on the blood vessel. The instrument comprises a pressure gauge 40 mounted to the hemostat 10 which responds to pressure exerted by the pressure pad 20 against the artery. The indicating instrument 39 may, however, comprise electronic pressure sensing apparatus to give an accurate indication of the pressure exerted against the artery, and a means of indicating blood pressure in the artery (not shown), as depicted by a second indicator gauge 41.

In a preferred embodiment, the hemostat mounting fixture 11 comprises a substantially flat base 44 to which a pair of elongate cylindrical support members 46 are attached and are extended upwardly. The upper ends 48 of the support members 46 are engaged and rigidly held by a cap 50 to maintain dimensional rigidity. A body member 52 slidably engages the support members and is slidable therewith in a lengthwise direction by means of bearing elements, such as ball slides 54, shown in phantom view in FIG. 1.

The fine-threaded screw 32 is rotatably attached to the cap 50 to allow turning movement of the screw while restricting longitudinal movement relative to the cap 50 and support members 46. The screw 32 is threaded into the body member 52 to provide a fine, substantially infinite adjustment of the body member 52 relative to the support members 46 and base 44. A handle 56 is provided at the upper end of the screw 32 above the cap 50, for convenient turning of the screw 32 by a physician or technician.

The pressure pad holding member 18 is attached between the distal ends 16 of the extending arms 12 and is vertically movable therewith. The holding member 18 may be vertically moved to selected positions provided by the detent pin 28 engaging one of the number of detent holes 29 formed in the holding member 18. The holding member 18 is prohibited any movement other than a vertical movement relative to the supporting arms 12. A pedestal 70 is provided in the lower end of the holding member 18 to which the pressure pad 20 is connected. The pedestal 70 protrudes from a central opening 72 formed through the holding member 18, as is shown in FIG. 1. The pedestal 70 acts as a piston to move fluid or air contained within the central opening relative to the opening 72 at the upper end of the holding member 18. The pressure gauge 40 is attached at the upper opening to provide an indication of movement of the pressure pad 20 relative to the end of the holding member 18, which movement corresponds to a pressure or contact force applied against the blood vessel. A biasing means (not shown) may be positioned within the central opening 72 to urge the pedestal 70 and pressure pad 20 from the holding member 18.

A pair of pivotal plates 58 are mounted to the body member 52 by a hinge pin 60 with one plate 58 being on each side of the body parallel to a plane through support the members 46. The hinge pin 60 is positioned through the body member 52 and pivot plates 58 at a forward position, allowing the mass of the plates 58 rearwardly of the hinge pin 60 to act as a counterweight for pivotal movement of the plates 58 about the hinge pin 60. A slot 62 is formed generally horizontally and longitudinally through each plate 58 to recieve an arm 12 which is cantilevered outwardly therefrom. Each arm 12 is slidable relative to the pivot plate 58 through the slot 62 to provide for horizontal adjustment of their distal ends 16 relative to the mounting fixture 10. The arms 12 are held in a desired position by a set screw 64 on each plate. A brace 66 is provided beween the distal ends 16 of the arms 12 to space and support them.

Figure 3:
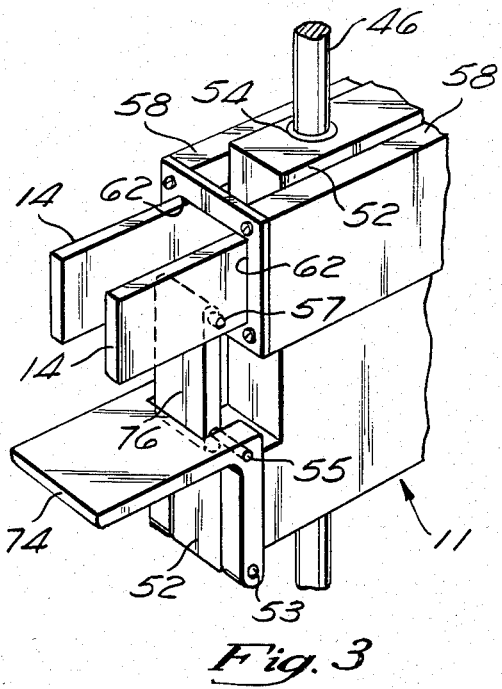
FIG. 3 is a view illustrating a lever and linkage for pivoting cantilevered arms.

A lever 74 and adjacent linkage 76, shown in FIG. 3, are coupled between the body member 52 and the rearward ends of the pivot plates 58 to direct pivotal movement of the extending arms 12 and the pressure pad 20 in the holding member 18, about the hinge pin 60 through the pivot plates 58. The lever 74 is pivotally mounted to the body 52 by pin 53. Linkage 76 is connected to lever 74 by pin 55 and connected to pivot plates 58 by pin 57. The lever 74 further provides for an emergency release of pressure exerted by the pressure pad 20 on the blood vessel, and allows the hemostat 10 to be quickly and easily removed should occasion arise, by simply moving the lever 74 to pivot the arms 12 and the pressure pad 20 upwardly and out of the way, as shown in FIG. 4.

When used, the hemostat 10 is positioned adjacent to a patient, with the arms 18 and pressure pad 20 pivoted upwardly. The base 44 is positioned beneath the portion of the body in which the artery to be catheterized extends with the arms 18 and pressure pad 20 extending over the proposed entry site. Prior to initiation of the surgical procedure, the hemostat 10 is adjusted into position to apply pressure to he artery. The pressure pad 20 is preferably located at a position upstream of the entry site of the catheter so that the puncture which is made to insert the catheter may be clearly visible to the attending physician for observance of clot formation and hemostasis.

Figure 4:
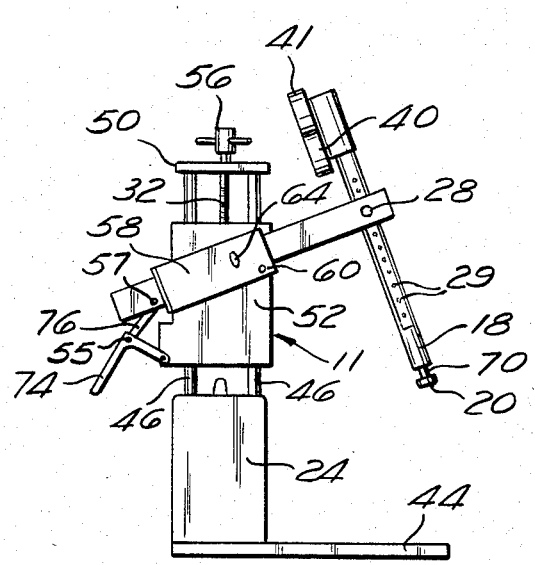
FIG. 4 is a side view of a hemostat showing a pressure pad and supporting arm in raised position.

The adjustment process is accomplished by pivotally lowering the arms 18 and pressure pad 20 until the lever 74 directing the rearward end of the pivotal movement is in locking position, shown if FIG. 4. Horizontal adjustment of the pressure pad 20 to properly place the pressure pad 20 above the blood vessel is accomplished by sliding the arms 18 relative to the pivot plates 58 and locking the set screw 64 to retain the position of the arms. The pressure pad holding member 18 is then vertically adjusted to the desired detent position 29 so as to place the pressure pad 20 in proximity to the blood vessel whose flow it must restrict. The fine screw adjustment 30 is then to be used by turning the handle 56 above the cap 50 at the top of the support members 46 to lower the pressure pad 20 into engagement it with the blood vessel. Advantageously, the handle 56 is turned while the physician or technician observes both the indication of pressure on the pressure gauge 40 and listens to the flow indication of blood flow provided by the audible output signal, until desired restriction of the blood vessel is obtained, without collapsing the vessel.

Upon completion of the catheterization procedure and as the catheter is withdrawn, the pressure pad 20 may be quickly and accurately applied to control blood flow through the blood vessel, and thus bleeding at the puncture site, by moving the lever 74 into locking position to pivot the pressure pad 20 into contact with the blood vessel in the pre-adjusted position. Again, fine adjustments may be made to provide a calibrated pressure to control the blood flow through the artery by using the fine thread adjustment 30. Once accurate adjustment is accomplished, the physician or technician may then proceed with other needed tasks while listening to the blood flow pulses as detected by the blood flow sensor 21 and audibly produced by the signal processor 24.

A significant feature of this invistion is that adequate blood flow through the blood vessel to lower extremities is always assured. If any change in blood flow through the artery should occur, it will become immediately apparent to the personnel in the area by a change in the sound provided by the signal processor 24. Emergency action can then be immediately taken. Personnel, however, may normally continue about their duties without maintaining supervision of the hemostate other than listening to the signal provided in response to blood flow through the artery.

Should an emergency occur, the hemostat 10 may be quickly removed by a simple unlocking of the lever 74 to upwardly pivot the pressure pad 20 and arms 12 out of the way to remove the hemostat 10 from the patient.

Figure 5:
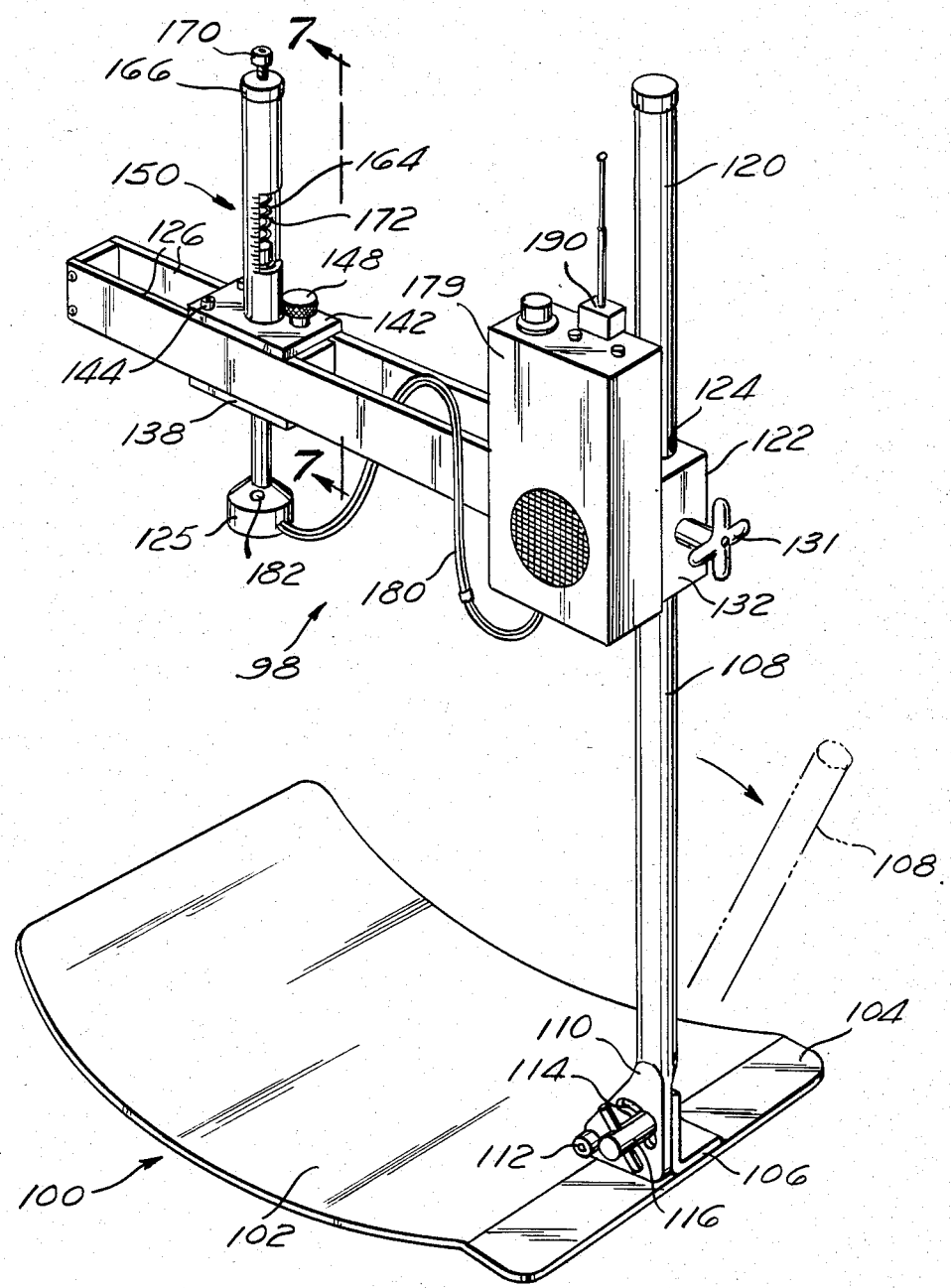
FIG. 5 is a rear perspective view of a second embodiment of a hemostat according to the invention.
Figure 6:
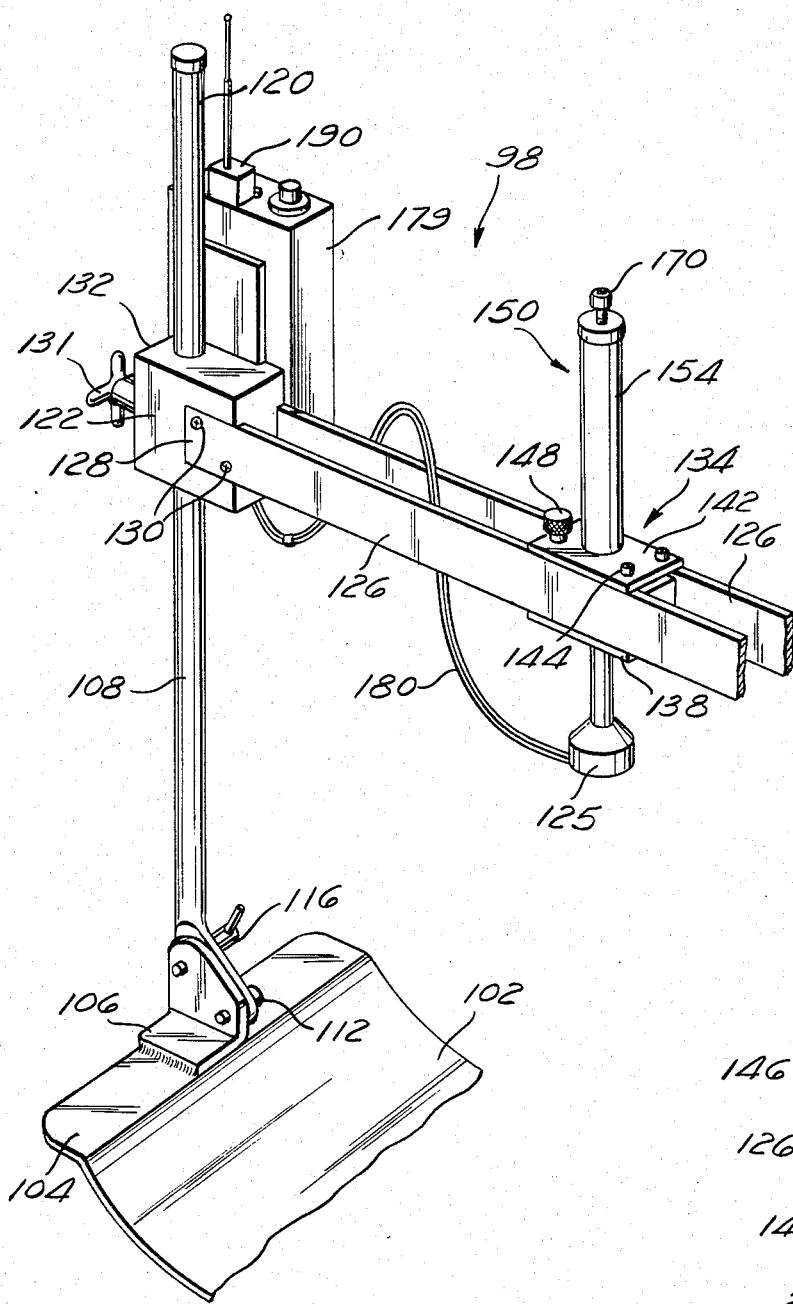
FIG. 6 is a forward perspective of the apparatus of FIGURES.
Figure 7:
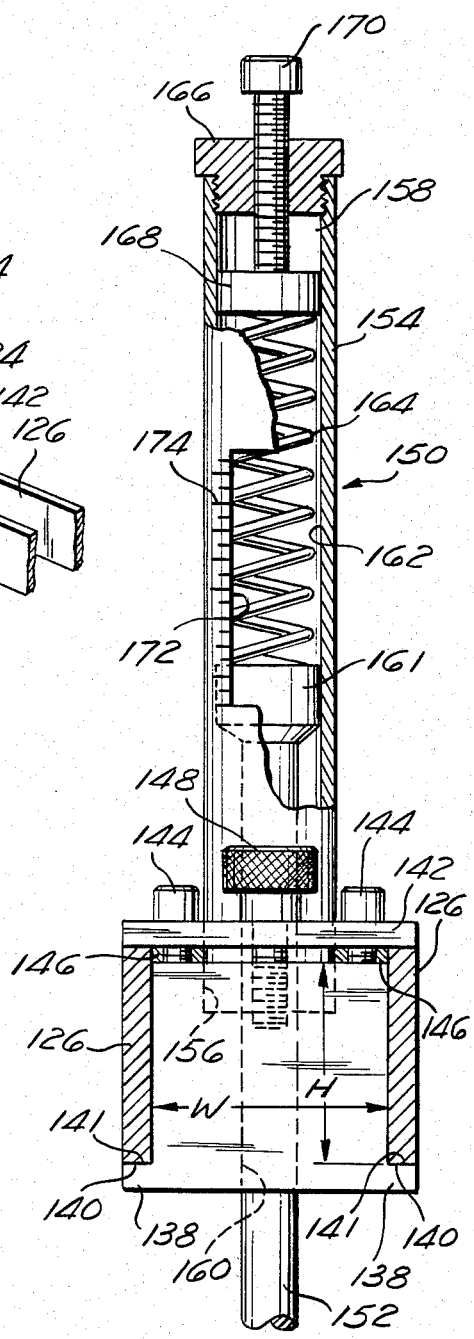
FIG. 7 is a cross sectional view taken along line 7—7 of FIG. 6.

FIGS. 5 through 7 illustrate a second preferred embodiment of a hemostat 98 including blood flow sensor 21. Referring first to FIG. 5, the hemostat 98 comprises a support plate 100 having a slightly curved portion 102 for placement below a patient's body to position the hemostat 98 in relation to the body of a patient during post-operative periods when the hemostat 98 is used to assist hemostasis. One end of the support plate 100 is provided with a flat portion 104 to which a bracket 106 is fastened by any suitable means such as welding or common threaded fasteners. An upright support member 108 is pivotally attached to the bracket 106 by a bolt or a hinge pin 112 and is allowed pivotal movement both toward and away from the support plate 100. A flat lower end 110 of the support member 108 is pivotally attached to the bracket 106 by the hinge pin 112 to provide pivotal movement between the upright support member 108 and the support plate 100. The flat end 110 of the support member 108 includes an arcuate slot 114 therein through which a wing bolt 116 extends to connect the support member 108 to the support plate 100. The wing bolt 116 passes through the slot 114 and is threaded into the bracket 106 so that when tightened, the wing bolt 116 will apply a compressive force between a flat portion 110 of the support member 108 and the bracket 106 to provide frictional engagement between the bracket 106 and support member 108 to hold the support member 108 in the desired pivotal position An upwardly extending portion 120 of the support member 108 is generally cylindrical in shape. Preferably, the support member 108 is comprised of a hollow cylindrical tube which has its lower end flattened and machined to provide the described features. A mounting block 122 is slidably positioned over the upper portion 120 of the upright support member 108. The mounting block 122 includes a bore 124 of a size slightly larger than the diameter of the cylindrical upper portion 120 of the support member 108, which extends through the bore 122 of the mounting block 122 for a loose sliding fit, while providing sufficient rigidity of the mounting block 122 on the upright member for substantially inflexible support. Adjustment of the position of the mounting block 122 on the support member 108 provides a coarse adjustment of a pair of arms 126, which extend over the wound site.

The pair of arms 126 are connected to and extend in spaced relation from the mounting block 122 in cantilever fashion. The arms 126 engage mating recesses 129 formed in the sides of the mounting block 122, as shown in FIG. 6. The arms 126 are attached within the recesses 128 by threaded fasteners 130. A wing screw 131 is threaded through an opposing end 132 of the mounting block 122 for engagement with the upright support member 108 to control movement of the mounting block 122 relative to the support member 108 and to hold the mounting block 122 in adjusted position on the upright support member 108. Loosening wing screw 131 permits adjustment of the position of the mounting block 122 along the length of the support member 108 and permits rotation of the mounting block 122 about the axis of the support member 108 to facilitate movement of the arms 126 adjacent to or away from an artery.

A pressure pad holding member 134 is slidably mounted between the arms 126. With reference to FIG. 7, the holding member 134 comprises a block 136 which has a generally rectangular cross section. The block 136 is sized to have a width slightly smaller than the spacing between the arms 126 for easy sliding engagement therebetween. The block 136 is positioned between the arms 126 with a lip 138 protruding from a lower portion of each side of the block 136 to engage a lower edge 140 of the arms 126. The height of the block 136 above the upper face 141 of the protruding lips 138 is slightly less than the height of the arms 126. A plate 142 of rectangular shape having the same length of the block 136, though slightly wider, is fastened by threaded fasteners 144 to the upper portion of the block 136 when the block 136 is inserted between the arms 126 to capture the block 136 between the arms 126 for sliding movement along the length thereof. The plate 142 is attached at one end by threaded fasteners 144 and spaced by spacers 146 from the upper surface of the block 136 so that the distance between the upper surface 141 of the protruding lip 138 and the lower surface of the plate 142 is slightly larger than the height of the protruding arms 126 to provide for easy sliding movement. A thumb screw 148 extends through the plate 12 at an opposing end and is threaded into the block 136 so that when the thumb screw 148 is tightened, the plate 142 is deflected toward the block 136, decreasing the distance between the upper surface 141 of the protruding lip 138 and the lower surface of the plate 142 to apply force to the arms 126 between the lip 138 and the plate 142. The frictional engagement between the arms 126 and the plate 142 and block 136 holds the pressure pad holding member 134 in adjusted position. Adjustment of the position of the pressure pad holding member 134 thus provides accurate placement of a pressure pad 125 over a selected artery of the patient. The pressure pad 125 includes a sensor 21 of the type described with reference to FIG. 1.

Continuing reference to FIG. 7, a pressure regulating assembly 150 includes a cylindrical pedestal 152 for mounting the pressure pad 125 to the block 136. The pressure regulating assembly 150 comprises a tubular member 154 which is press fitted into a counter bore 156 in the block 136, to position the tubular member 154 in perpendicular relation to the arms 126. The pedestal 152 is inserted into an interior passage 158 of the tubular member 154, and through a sized bore 160 formed through the block 136 concentrically with the counter bore 156 to position the pedestal 152 to support the pressure pad 125. The pedestal 152 and the bore 160 formed through the block 136 have a sliding fit to allow sliding movement of the pedestal 152 within the block 136.

The uppermost portion of the pedestal 152 has an enlarged cylindrical portion 161 slightly smaller in diameter than the interior passage 158 in the tubular member 154 to maintain guided sliding engagement of the upper portion 161 of the pedestal 152 within the passage 158. A spring 164 is positioned above the pedestal 152 to apply force through the pedestal 152 to the pressure pad 125 to apply pressure to an artery on which the pressure pad 125 is placed.

An upper spring seat 168 is positioned over the spring 164 to position the upper face of the spring 164 in a desired vertical position within the tubular member 154. An end cap 166 is threaded into the uppermost end of the tubular member 154. A screw 170 is threaded through the end cap 166 with a lower end of the screw 170 engaging the upper spring seat 108 to position the upper spring seat 108 in a desired position within the tubular member 154. The screw 170 compresses the spring 164, so that the spring 164 will apply force to the pedestal 152 and the pressure pad 125. Therefore, as the screw 170 is turned and screwed into the end cap 66, the upper spring seat 168 is lowered within the tubular member 154 to compress the spring 164 to provide increased pressure to the pedestal 152 and the pressure pad 125. Adjustment of the screw 170 to control the compression of spring 164 provides an infinitely variable fine adjustment of the pressure applied to an artery positioned below the pressure pad 125.

The tubular member 154 includes a window 172 intermediately positioned between the upper and lower ends thereof, through which the enlarged portion 161 of the pedestal 152 may be viewed. A scale calibration 174 is positioned immediately adjacent the window 172 so that the pressure aplied by the pedestal 152 may be ascertained by viewing the position of the enlarged portion 161 relative to the calibration scale through the window 172.

Figure 8:
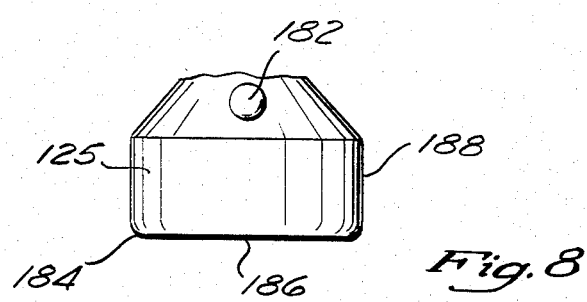
FIG. 8 is an elevation view of a pressure pad and indicator light.

The pressure pad 125 is mounted to the lowermost portion of the pedestal 152 and may be provided in a number of varied sizes for adaptation to the size of artery in which blood flow restriction is desired. Referring to FIG. 8, the lower portion of the pressure pad 125 is generally cylindrical, but the edge 184 between the face 186 and the side 188 of the pressure pad 125 may be slightly curved to avoid having a sharp edge pressing against the patient's body.

Referring to FIGS. 5, 6, and 8, the hemostat 98 may conveniently include a light indicator 182, which is connected to the sensor 21 in the pressure pad 125. The light indicator 182 flickers in response to pulsating blood flow to provide a visual indication of whether the pressure pad 125 is on an artery and to indicate the blood flow rate through the artery. The light indicator 182 begins to flicker to indicate proper placement of the pressure pad 125 over an artery and continues to flicker when the pressure pad 125 is pressing on the artery in response to pulsating blood flow. The light indicator 182 ceases to flicker to indicate that the pressure pad 125 is removed from the artery or that blood flow through the artery has stopped, which may indicate excessive pressure between the pressure pad 125 and the artery.

The blood flow sensor 21 is connected to an audible control unit 179 by a pair of wires 180. The audible control unit 179 includes a signal processor (not shown in FIG. 8), as described with reference to FIGS. 1 and 2. The audible control unit 179 produces a sound output which varies in pitch or volume in response to changes in blood flow through an artery adjacent the pressure pad 125.

Referring to FIGS. 5 and 6, the hemostat 98 may include a low-power radio frequency transmitter 190 connected to the output of the sensor 21. The transmitter 190 may be conveniently mounted to the audible control unit 179. Transmitter 190 outputs a low-power radio frequency signal which is capable of being received by a portable receiver (not shown) several feet away from transmitter 190, such as in a hospital room adjacent the room in which the hemostat 98 is in use. The receiver preferably converts the radio frequency signal into an audible signal. Thus, the transmitter 190 enables hospital personnel to monitor the progress of hemostasis without being in the same room as the patient.

Table I indicates the height, weight, and hemostasis time for 21 patients upon whom the invention was tested. Ordinary catheters were inserted in patients 1 through 9, and 11-14 who had normal blood clotting rates. The blood of patient 10 clotted at a rate which was only 29% of the normal blood clotting rate; therefore, the hemostasis time for this patient was much longer than the typical ten minute hemostasis time for a patient whose blood clots at the normal rate. Achieving hemostasis in patient 10 would have been extremely difficult using ordinary methods and would have required the constant attention of trained personnel. Patients 15-21 received an angioplasty which requires the insertion of a catheter which is much larger than the catheters used on patients 1-14. Of the group of patients who received an angioplasty, only patient 20 had an unusually long hemostasis time. Patient 20 had received 10,000 units of Heparin, which prolonged the hemostasis time.

TABLE 1

| Patient | Height | Weight | Hemostasis Time |
|---|---|---|---|
| 1 | 5'8" | 143½ lb | 10 minutes |
| 2 | 5'0" | 149 | 10 |
| 3 | 5'5" | 151 | 10 |
| 4 | 5'7" | 194 | 10 |
| 5 | 5'10" | 153 | 10 |
| 6 | 6'½" | 212 | 10 |
| 7 | 5'9" | 146 | 10 |
| 8 | 5'7" | 103 | 10 |
| 9 | 6'3 | 234½ | 10 |
| 10 | | | 50 |
| 11 | 5'6" | 161 | 10 |
| 12 | 5'8" | 162 | 15 |
| 13 | 5'2" | 144 | 10 |
| 14 | 5'3" | 104 | 7 |
| 15 | 5'8" | 138 | 10 |
| 16 | 5'7" | 160 | 10 |
| 17 | 6'4" | 268 | 20 |
| 18 | 6'6" | 192 | 10 |
| 19 | 5'3" | 113 | 10 |
| 20 | 5'1" | 128 | 35 |
| 21 | 5'7" | 168 | 20 |

Although the invention is described in detail with reference to specific embodiments, modifications may be made which are within the scope and spirit of the invention. Accordingly, the scope of the invention is limited only by the appended claims.

What is claimed is:

1. A hemostat for controlling the flow of blood in a blood vessel to a puncture site in the body, comprising:
   a mounting fixture;
   an arm adjustably mounted to said mounting fixture;
   a non-inflatable pressure pad mounted to said arm for applying pressure to said blood vessel at a location upstream from said puncture site;
   an electronic sensor mounted with said pressure pad for sensing blood flow through said vessel past said pressure location, said sensor being responsive to the rate of blood flow through said vessel, and providing an output signal to indicate changes in blood flow through said vessel to attending personnel;
   means for adjusting the force applied by said pressure pad to said blood vessel so that blood flow through said blood vessel may be accurately controlled; and
   means for indicating the force applied by said pressure pad to said blood vessel.

2. A hemostat for restricting flow of blood in a blood vessel comprising:
   a mounting fixture;
   an arm cantilever mounted to said mounting fixture and movably adjustable thereto;
   non-inflatable means for applying pressure to said blood vessel, said means removably attached to the end of said arm, and selectable in size to approximate the size of said vessel in which flow is to be restricted, and said means further comprising non-occlusive means for electronically sensing the rate of blood flow through said blood vessel; and
   means for adjusting pressure applied to said blood vessel by said pressure applying means, said pressure adjusting means adapted to determine the pressure applied to said blood vessel and maintain said pressure constant to obtain a substantially constant restriction of said blood vessel, said adjusting means prohibiting movement of said pressure applying means except when said adjustment means is actuated by an operator.

3. The hemostat of claim 2 further comprising means for indicating the pressure applied to said blood vessel by said pressure applying means.

4. The hemostat of claim 2 wherein said arm is pivotally mounted to said mounting fixture, said arm being adapted to be pivotally moved to position said pressure applying means to exert a clamping force against said blood vessel to restrict flow therethrough.

5. The hemostat of claim 4 wherein said pivotal movement of said arm is actuated by a lever and a linkage coupled between a portion of said arm and a portion of said mounting fixture, said lever providing for quick and immediate release of said pressure applying means from flow restricting position in event of an emergency situation.

6. The hemostat of claim 2 wherein said means for adjusting said pressure applying means comprises:
   means for making large segmented adjustments of said pressure applying means, and means for making small, substantially infinitely variable adjustments of said pressure applying means, said large and small adjustment means prohibiting movement of said pressure applying means except when said adjustment means is actuated by an operator.

7. The hemostat of claim 2 wherein said blood flow sensing means includes audible means for indicating changes in blood flow through said blood vessel.

8. The hemostat of claim 2 wherein said blood flow sensing means includes visual means for indicating changes in blood flow through said blood vessel.

9. The hemostat of claim 2 wherein said blood flow sensing means includes a chart recorder for recording blood flow rate measurements through said blood vessel.

10. The hemostat of claim 2 further comprising means for releasing said arm, said release means being adapted to quickly move said arm from a pressure applying position in an emergency.

11. The hemostat of claim 2 wherein said pressure applying means comprises a pressure pad holding member attached to an outer end of said arm, said holding member having a central opening formed longitudinally therethrough, and a pedestal movably positioned in one end of said central opening and protruding from said holding member, and a pressure pad removably attached to said pedestal.

12. The hemostat of claim 11 further comprising means for indicating the pressure exerted by said pressure pad on said blood vessel.

13. The hemostat of claim 12 wherein said indicating means is attached to said pressure pad holding member to communicate with said central opening therein, said indicating means responding to a fluid movement through said central opening resulting from movement of said pedestal position in one end of said central opening.

14. A hemostat for controlling flow of blood through a blood vessel comprising:
a mounting base;
at least one upright support member;
a body member slidably engaged with said support member;
at least one arm pivotally attached to said body member, said arm being adjustable relative to said body member to position a distal end of said arm in a selected position relative to said body member;
means for applying pressure to said blood vessel adjustably attached to said distal end of said arm, said pressure applying means comprising:
a non-inflatable pressure pad approximating the size of said blood vessel;
a pedestal for removably mounting said pressure pad;
a holding member for movably mounting said pedestal and said pressure pad; and
means for adjusting said holding member relative to said arm to position said pressure pad relative to said blood vessel;
electronic means for sensing blood flow rate through said blood vessel, said sensing means comprising a sensor positioned with said pressure pad, and audible signal means responsive to changes in blood flow through said blood vessel connected to said sensing means;
means for holding said arm and said pressure pad in position to exert pressure against said blood vessel, said means providing for quick release to pivot said arms away from pressure applying position; and
means for finely adjusting said pressure pad relative to said mounting base, said means prohibiting movement of said pressure applying means except when said adjustment means is actuated.

15. A hemostat for restricting flow of blood in a blood vessel, comprising:
a support plate;
a support member pivotally mounted to said support plate for movement in a plane substantially perpendicular to said plate;
an arm extending from said support member and movable relative thereto in two mutually perpendicular planes;
non-inflatable means for applying pressure to said blood vessel;
non-occlusive means for electronically sensing the rate of blood flow through said blood vessel when pressure is applied;
means for adjusting pressure applied to said blood vessel by said pressure applying means, said adjusting means being adapted to determine the pressure applied to said blood vessel to obtain a substantially constant restriction of said blood vessel; and
means for adjustably mounting said pressure applying means to said arm, said adjustable mounting means being adapted to provide infinitely selective spacing between said pressure applying means and said support member.

16. The hemostat of claim 15 further comprising means for adjusting pivotal movement of said support member relative to said support plate.

17. The hemostat of claim 15 further comprising means for indicating the pressure applied to said blood vessel by said pressure applying means.

18. The hemostat of claim 15 further comprising means for releasing said pressure applying means in an emergency, said release means being adapted to facilitate movement of said support member and said arm mounting said pressure applying means in an emergency.

19. The hemostat of claim 15 wherein said means for adjusting said pressure applying means comprises means for making large segmented adjustments of said pressure applying means, and means for making small, substantially infinitely variable adjustments of said pressure applying means, said large and small adjustment means resisting movement of said pressure applying means except in response to actuation by an operator.

20. The hemostat of claim 15 wherein said blood flow sensing means includes audible means for indicating changes in blood flow through said blood vessel.

21. The hemostat of claim 15 wherein said blood flow sensing means includes visual means for indicating changes in blood flow through said blood vessel.

22. The hemostat of claim 15 wherein said pressure applying means comprises a pressure pad holding member slidably attached to said arm, said pressure pad holding member having a central opening formed therethrough, a pedestal removably positioned through said opening and protruding from said holding member, and a pressure pad removably attached to said pedestal.

23. The hemostat of claim 22 wherein said pressure pad includes means for sensing blood flow, said sensing means being positioned within a central portion of said pressure pad.

24. The hemostat of claim 23 wherein said means for sensing blood flow is adjustable relative to a lower surface of said pressure pad.

25. The hemostat of claim 15 further comprising means for indicating the pressure exerted by said pressure pad on said blood vessel.

26. A hemostat for controlling blood flow through a blood vessel comprising:
a mounting base;
at least one support member;
a body member slidably engaged with said support member;
at least one arm extending from said body member, said arm and said body member being adjustable with said support member to position a distal end of said arm in a selected position relative to said mounting base;
means for applying pressure to said blood vessel adjustably mounted to a distal end of said arm, said pressure applying means comprising:
a holding member movably mounted to said arm;
a pedestal movably mounted to said holding member;
a non-inflatable pressure pad mounted to an end of said pedestal;
means for adjusting said holding member relative to said arm, to position said pressure pad relative to said blood vessel;
electronic means for sensing blood flow rate through said blood vessel, said sensing means comprising a sensor positioned with said pressure pad, and audible signal means responsive to changes in blood flow through said blood vessel connected to said sensing means;

means for holding said pedestal and said pressure pad in position to exert pressure against said blood vessel;

means for providing an indication of pressure applied to the blood vessel;

means for holding said arm and said pressure pad in position to exert pressure against said blood vessel, said means providing for a quick release to pivot said arms away from pressure applying position; and means for adjusting said pressure pad relative to said mounting base, said adjusting means selectively applying force to said pressure pad when said adjustment means is actuated.

27. The pressure applying means of claim 26 further including means for adjusting said means for sensing blood flow rate through said blood vessel in said pressure pad to selectively position said sensing means relative to a lower surface of said pressure pad.

* * * * *